United States Patent [19]

DesJardins et al.

[11] Patent Number: 4,817,618

[45] Date of Patent: Apr. 4, 1989

[54] RANGE-CONTINUITY ANTI-ALIASING

[75] Inventors: Philip A. DesJardins, Seattle; Jeffry E. Powers, Rainbridge Island, both of Wash.

[73] Assignee: Advanced Technology Laboratories, Inc., Bothell, Wash.

[21] Appl. No.: 120,214

[22] Filed: Nov. 12, 1987

Related U.S. Application Data

[63] Continuation of Ser. No. 062,359, Jun. 12, 1987, abandoned, which is a continuation of Ser. No. 739,254, May 30, 1985, abandoned.

[51] Int. Cl.[4] .................................................. A61B 8/06
[52] U.S. Cl. ............................ 128/661.09; 73/861.25
[58] Field of Search ............. 128/663, 661.07, 661.08, 128/661.09; 73/861.25, 602; 367/90, 94; 342/402, 405, 418, 99

[56] References Cited

U.S. PATENT DOCUMENTS

| 4,103,679 | 8/1978 | Aronson | 128/663 |
| 4,476,874 | 10/1984 | Taenzer et al. | 128/663 |
| 4,534,357 | 8/1985 | Powers | 128/663 |
| 4,607,642 | 8/1986 | Powers | 128/663 |

*Primary Examiner*—Ruth S. Smith
*Attorney, Agent, or Firm*—Christensen, O'Connor, Johnson & Kindness

[57] ABSTRACT

A Doppler blood velocity measuring device is described which includes anti-aliasing circuitry. The anti-aliasing circuitry is based upon the use of a multigate Doppler unit which receives Doppler shift frequency information from various depth ranges. Thereafter, the Doppler frequencies received are corrected by adding a correction frequency to the perceived Doppler frequency with the correction frequency selected based on the assumption that blood flow velocity cannot change drastically between adjacent depths.

8 Claims, 1 Drawing Sheet

RANGE-CONTINUITY ANTI-ALIASING

This application is a continuation application based on prior copending application Ser. No. 062,359, filed 6/12/87 now abandoned which is a continuation application based on prior application Ser. No. 739,254 filed 5/30/85, now abandoned.

BACKGROUND OF THE INVENTION

The present invention relates to an improved medical ultrasound Doppler unit of the type used for measuring velocity of blood flow.

Pulsed Doppler velocimeters can discern only a limited range of Doppler-shifted frequencies. This limitation arises from insufficient time-sampling of the Doppler signal. Pulsed Doppler velocimeters sample a Doppler-shifted signal at a single arbitrary depth, a depth determined by the delay between the insonifying pulse and the sampling time. This sampling, performed at a rate called the Pulse Repetition Frequency (PRF), limits the maximum unambiguously discernable Doppler-shifted frequency, and, therefore, the maximum discernable velocity.

The Nyquist Sampling Theorem implies that a pulsed Doppler velocimeter can unambiguously discern only those Doppler-shifted frequencies which are between $-PRF/2$ and $+PRF/2$. Any Doppler-shifted frequency outside of this interval (hereafter called the "Nyquist interval") will be aliased, that is, it will appear to be at a frequency that is inside this interval. Without additional information, the pulsed Doppler velocimeter cannot discern whether a perceived Doppler-shifted frequency is actually within the Nyquist interval or whether it is an alias of a frequency outside of this interval.

Mathematically, the perceived frequency, $f_p$, of a signal sampled at $f_s$ and having a true frequency, $f_t$, is found by:

$$f_p = f_t - f_s * \text{ROUND}(f_t/f_s) \quad \text{(eq 1)}$$

where ROUND(X) is a function which rounds the number inside the parentheses, i.e., ROUND(X) will be an integer which is equal to the greatest integer in X, plus 1 if the remaining fractional part is greater than or equal to 0.5.

For pulsed Doppler velocimeters, this equation is written as:

$$f_p = f_6 - \text{PRF} * \text{ROUND}(f_t/\text{PRF}) \quad \text{(eq 2)}$$

Thus, the perceived frequency is always within the Nyquist interval. If the true frequency is also between $-PRF/2$ and $PRF/2$, then no aliasing occurs, and the perceived frequency is the true frequency. If the true frequency is outside the Nyquist interval, then the true frequency appears to be the perceived frequency as found in (eq 2). The ROUND function in the above equation can alias several possible true frequencies ($f_t$'s) onto the same perceived frequency $f_p$. Accordingly, there is no direct way to determine whether the perceived frequency is the true frequency of one of many possible aliases.

Methods used heretofore to circumvent the aliasing problem included using continuous wave (CW) Doppler, a common technique. However, continuous wave Doppler loses all range resolution.

Another approach is to decrease the transmitted frequency in order to proportionally decrease the Doppler-shifted frequency. A disadvantage of this common technique is the problem of decreased scattering and decreased partial resolution.

Increasing the PRF in order to increase the Nyquist interval is also a commonly used technique However, it is subject to range ambiguities. The signal from a desired range cell of depth, d, is sampled by delaying the sample with respect to the insonifying pulse by a time, t, found by:

$$t = 2d/c, \quad \text{(eq 3)}$$

Where c is the propagation velocity of the insonifying signal. Equation 3 does not separate the desired range's signal from signals coming from deeper ranges (which were insonified by prior pulses). That is, it also receives signals from ranges at the following depths:

$$d(n) = (c/2) * (t + nT), \quad \text{(eq 4)}$$

Where T is the pulse repetition period ($=1/\text{PRF}$), and n is an integer which is greater than or equal to 1.

This interference is not a problem when T is sufficiently large (the PRF is sufficiently low). In such case, the unwanted range cells are so deep that their signals are sufficiently attenuated by the propagating medium and, therefore, are so weak that they do not interfere with the desired signal. However, as the PRF increases, the unwanted ranges move closer to the insonifying source, and their signals become strong enough to interfere with the desired signal.

This interference has been exploited to advantage by the high-PRF or "extended range" concept, whereby the desired range is not the closest received range but rather one of the deeper ones. This technique assumes, however, that the signals coming from the shallower, unwanted ranges are negligible.

The main disadvantage of the extended-range concept is that we do not know that the interference from undesired ranges are negligible.

Another approach which was used heretofore involves estimating the Doppler frequency f(i) at a time t(i), and assuming that estimates at times t(j), near t(i), are also close to (within $\pm PRF/2$ of) this estimate. If a perceived frequency, $f_p(j)$, is outside this range, it is replaced with the "most-likely" true frequency, $f_{ml}(j)$. $f_{ml}(j)$ is chosen from all the possible true frequencies which alias to the perceived frequency $f_p(j)$. The one chosen is the one closest to f(i) and is found by the following formula:

$$f_{ml}(j) = f_p(j) + \text{PRF} * \text{ROUND}((f_{ml}(i) - f_p(j))/\text{PRF}) \quad \text{(eq 5)}$$

The baseline estimate, f(i), is periodically updated in order to track non-stationary Doppler spectra (such as caused by the variation of blood velocity distribution over the cardiac cycle, as seen by Doppler blood velocimeters).

One disadvantage of this approach is that the original baseline estimate must not be aliased, or else the future estimates will be corrupted.

A second disadvantage of this method is that the technique assumes that the time between frequency estimates is sufficiently short such that the difference between the true frequencies $f_t(j)$ and $f_t(i)$ is within the Nyquist interval. If the Doppler spectrum changes sufficiently between updates, then future estimates will be corrupted.

SUMMARY OF THE INVENTION

Range-continuity anti-aliasing corrects for aliasing by first making a frequency estimate, f(i), at an arbitrary range cell r(i). Any perceived frequency $f_p(j)$ estimated at a nearby range cell r(j) is compared to f(i) and corrected for aliasing according to equation 5. The most likely frequency, $f_{ml}(j)$, at range cell r(j) is found by:

$$f_{ml}(j) = f_p(j) + PRF \cdot ROUND((f_{ml}(i) - f_p(j))/PRF) \quad (eq\ 6)$$

After $f_{ml}(j)$ is calculated, the frequency estimates for ranges close to r(j) can be alias-corrected by extending the technique of equation 6. Thus, r(j) and $f_{ml}(j)$ become the new r(i) and f(i), respectively, and a new range is chosen as r(j).

By successively choosing the new range cells, the r(j)'s, further and further away from the original f(i), all range cells acquired by the Doppler velocimeter can be corrected for aliasing.

This technique assumes that the original f(i), called f(0), is correct to within ±PRF/2. This can be done by choosing a range r(0) where it is assumed there are no moving targets. The frequency f(0) estimated at this range is assumed to be within the Nyquist interval, and is set to $f_p(0)$.

Similarly, if the Doppler velocimeter determines that the signal coming from any arbitrary range cell has no significant Doppler information, then the correction circuitry assumes that the signal is noise and sets the most-likely frequency to be the perceived frequency.

This technique requires the ability to simultaneously acquire Doppler-shifted signals from multiple range cells. Accordingly, the use of this technique requires a "multigate Doppler" of the type described by A. P. G. Hoeks in a thesis entitled "On the Development of a Multi-gate Pulsed Doppler System with Serial Data Processing", submitted to the University of Linburg, Maastricht, the Netherlands.

This technique requires a frequency estimator that operates at any or all the acquired range cells. This frequency estimator calculates the perceived frequency $f_p$, a frequency which is within the Nyquist interval.

The disclosed technique assumes that the true Doppler-shifted frequency varies slowly in range. The distance between r(i) and r(j) must be sufficiently short such that the difference between the true frequencies, $f_t(i)$ and $f_t(j)$, is within ±PRF/2. This means there must be sufficient spatial sampling in range.

DETAILED DESCRIPTION OF THE PREFERRED EMBODIMENT

Figure 1:
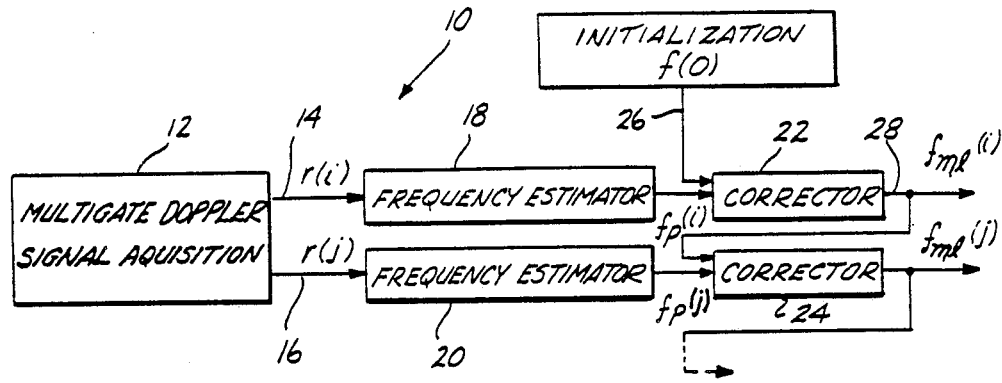
FIG. 1 shows anti-aliasing circuitry according to a first embodiment.

Referring generally to FIG. 1, a first embodiment of the present invention 10 is shown. The invention 10 is comprised of a multigate Doppler unit 12. As used herein, the term "multigate Doppler unit" refers to an apparatus which may be used to acquire Doppler signals at multiple depth ranges. Devices of this type have been used heretofore and are considered, for the purposes of this invention, to be well known to those of ordinary skill in the art. The outputs of the multigate Doppler unit 12 consist of Doppler signals at various depth ranges. Thus, an output signal at range i appears on a first line 14, and an output signal at range j on a second line 16. These output signals, are (i) and (j), respectively. These output signals go into frequency estimators 18, 20. A frequency estimator is a device capable of estimating frequency of the Doppler signal. The output of each of the frequency estimators 18, 20 is the perceived frequency $F_p(i)$ and $F_p(j)$, respectively and will be in the range of ±PRF/2. As discussed above, the perceived frequency may be aliased. Accordingly, the perceived frequency outputs of the frequency estimators 18, 20 are fed into frequency corrector circuits 22, 24. The job of the frequency corrector circuits 22, 24 is to correct the perceived frequency, $F_p$, by adding the proper multiple of the PRF which is found by using equation 6.

In accordance with the present invention, the proper multiple will be an integer which is found iteratively. In order to arrive at the most likely frequency, the assumption is made that the velocity in the selected depth range will not vary significantly from the velocity of the preceding depth range. This means that if the output of corrector 22 is $F_{ml}(i)$ then the output of corrector 24 will be $F_p(j)$ plus a multiple of PRF found by rounding the difference between $F_{ml}(i)$ and $F_p(j)$ to the integer corresponding to the nearest multiple of PRF. In general, each output frequency will be correct if two assumptions are correct. First, the blood flow must be within the sample depth and has not changed significantly from the blood flow in the adjacent sample depth, i.e., the Doppler signal is within ±PRF/2 of the Doppler signal of the adjacent sample depth. Second, since each correction is based upon the accuracy of the preceding frequency, at some point we have to assume that we have properly initialized a corrector. Accordingly, the present invention assumes that there is no movement in the shallowest range and the initial most likely frequency, $F_{ml}(0)$ of the first corrector 22 is set to $F_p(0)$ on line 26. Thereafter, $F_{ml}(i)$ on line 28 is used as the correcting frequency which is input into the corrector 24 to compute $F_{ml}(j)$.

Any time that intensity of the Doppler signal is weaker than a predefined threshold, the corrector assumes that there is no blood flow at the corrector depth and $F_{ml}$ out of that corrector will be set to $F_p$.

Figure 2:
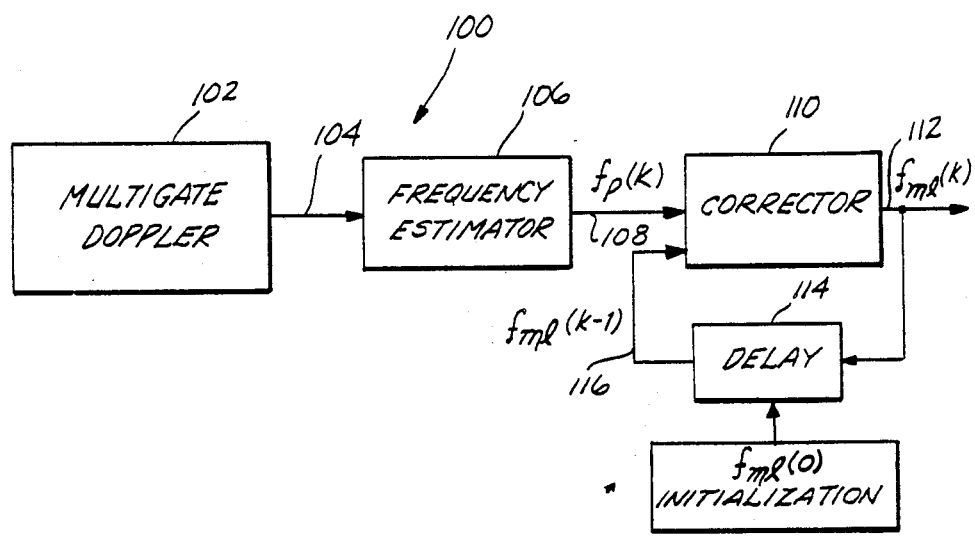
FIG. 2 shows anti-aliasing circuitry according to a second embodiment.

Referring now to FIG. 2, the preferred embodiment 100 of the present invention is shown. In the preferred embodiment 100 there is a multigate Doppler unit 102 which generates time-multiplexed samples of the Doppler signal which are sent via output line 104 into a frequency estimator 106. For example, the multigate Doppler unit 102 may start with the most shallow depth and then step deeper into successive sample groups from adjacent sample depths to provide a frequency estimator 106 with Doppler signals. The output of the frequency estimator 106 will be a perceived frequency $F_p(k)$ for each depth, k. That perceived frequency $F_p(k)$ is set into a corrector circuit 110 via line 108, and output of the corrector circuit 110 will be the most likely frequency at depth k, $F_{ml}(k)$ on line 112. $F_{ml}(k)$ is also set into a delay unit 114 which samples the $F_{ml}(k)$ and holds it while the multigate Doppler unit 102 steps into the next depth. Accordingly, the output of the delay unit 114 will be the most likely frequency at depth k−1 on line 116.

In accordance with the preferred embodiment of the invention 100, the assumption is made that at depth 0 there is no blood flow. Accordingly, the frequency $F_{mi}(0)$ is initialized to $F_p(0)$, and subsequent depths are adjusted to provide the most likely frequency thereafter.

We claim:

1. Anti-abasing circuit for use in a pulsed doppler ultrasound velocimeter comprising:
    (a) multigate doppler means including means for transmitting and receiving ultrasonic waves and means for providing doppler signals from a plurality of different range gates corresponding to a plurality of different sample depths;
    (b) frequency estimator means for receiving the doppler signals and for providing, for each range gate, a corresponding perceived frequency signal representing the perceived frequency of the doppler signal for the range gate; and
    (c) anti-aliasing means for receiving the perceived frequency signals and for providing an unaliased signal corresponding to each range gate, the anti-aliasing means including means for comparing, for each range gate, the perceived frequency signal corresponding to the range gate with the unaliased signal corresponding to a different range gate, and for modifying the value of the perceived frequency signal corresponding to the range gate to produce the unaliased signal corresponding to the range gate by reducing the difference between the unaliased signal corresponding to said different range gate and the perceived frequency signal corresponding to the range gate, and initialization means for providing an initialization signal such that for one range gate, the anti-aliasing means produces the corresponding unaliased signal by reducing the difference between the initialization signal and the perceived frequency signal corresponding to said one range gate.

2. The velocimeter of claim 1, wherein the multigate doppler means operates at a pulse repetition frequency PRF, and wherein the anti-aliasing means includes means for modifying the value of the perceived frequency signal to produce the unaliased signal by adding to the value of the perceived frequency signal the product of the PRF and a positive, negative or zero integer.

3. The velocimeter of claim 1, wherein the multigate doppler means provides the doppler signals as a time multiplexed series wherein successive doppler signals correspond to adjacent range gates, wherein the frequency estimator means provides the perceived frequency signals as a corresponding series of time multiplexed signals for adjacent range gates, and wherein the anti-aliasing means includes delay means for storing the unaliased signal for each range gate for use in the succeeding production of the unaliased signal for the succeeding range gate.

4. The velocimeter of claim 3, wherein the initialization means provides the initialization signal for the production of the unaliased signal for the first range gate.

5. An anti-aliasing method
for use with multigate doppler means that includes means for transmitting and receiving ultrasonic energy and means for providing doppler signals from a plurality of different range gates corresponding to a plurality of different sample depths, the method comprising:
    (a) providing, for each range gate, a corresponding perceived frequency signal representing the perceived frequency of the doppler signal for the range gate;
    (b) providing an unaliased signal corresponding to each range gate by comparing, for the range gate, the perceived frequency signal corresponding to the range gate with the unaliased signal corresponding to a different range gate, and modifying the value of the perceived frequency signal corresponding to the range gate to produce the unaliased signal corresponding to the range gate by reducing the difference between the unaliased signal corresponding to said different range gate and the perceived frequency signal corresponding to the range gate; and
    (c) providing an initialization signal such that for one range gate, the anti-aliasing means produces the corresponding unaliased signal by reducing the difference between the initialization signal and the perceived frequency signal corresponding to said one range gate.

6. The method of claim 5, wherein the multigate doppler means operates at a pulse repetition frequency PRF, and wherein the value of the perceived frequency signal is modified to produce the unaliased signal by adding to the value of the perceived frequency signal the product of the PRF and a positive, negative or zero integer.

7. The method of claim 5, wherein the doppler signals are provided as a time multiplexed series wherein successive doppler signals correspond to adjacent range gates, wherein the perceived frequency signals are provided as a corresponding series of time multiplexed signals for adjacent range gates, and wherein the unaliased signal for each range gate is stored for use in the succeeding production of the unaliased signal for the succeeding range gate.

8. The method of claim 7, wherein the initialization signal is provided for the production of the unaliased signal for the first range gate.

* * * * *